(12) United States Patent
Nakazawa et al.

(10) Patent No.: US 8,652,847 B2
(45) Date of Patent: Feb. 18, 2014

(54) CELLULAR TISSUE MICROCHIP AND METHOD OF FORMING CELLULAR TISSUE

(75) Inventors: Kohji Nakazawa, Kitakyushu (JP); Junji Fukuda, Kitakyushu (JP)

(73) Assignee: Kitakyushu Foundation for the Advancement of Industry, Science and Technology, Kitakyushu (JP)

(*) Notice: Subject to any disclaimer, the term of this patent is extended or adjusted under 35 U.S.C. 154(b) by 1514 days.

(21) Appl. No.: 11/665,817

(22) PCT Filed: Oct. 21, 2005

(86) PCT No.: PCT/JP2005/019427
§ 371 (c)(1),
(2), (4) Date: Apr. 19, 2007

(87) PCT Pub. No.: WO2006/046490
PCT Pub. Date: May 4, 2006

(65) Prior Publication Data
US 2008/0138900 A1 Jun. 12, 2008

(30) Foreign Application Priority Data
Oct. 29, 2004 (JP) ................................. 2004-315600

(51) Int. Cl.
*C12N 5/00* (2006.01)

(52) U.S. Cl.
USPC ..................... 435/402; 435/305.1; 435/305.2; 435/395

(58) Field of Classification Search
USPC ................................................. 435/395, 402
See application file for complete search history.

(56) References Cited

U.S. PATENT DOCUMENTS

| 5,202,227 A | 4/1993 | Matsuda et al. |
| 2002/0173033 A1 | 11/2002 | Hammerick et al. |
| 2002/0182633 A1* | 12/2002 | Chen et al. ............. 435/7.1 |
| 2004/0161744 A1* | 8/2004 | Moriya et al. .............. 435/6 |

FOREIGN PATENT DOCUMENTS

| EP | 0 402 718 A1 | 12/1990 |
| JP | A 10-029951 | 2/1998 |
| JP | B1 3020930 | 1/2000 |
| JP | A 2002-153260 | 5/2002 |
| WO | WO 03/044164 A2 | 5/2003 |

OTHER PUBLICATIONS

Ostuni, E et al. Selective deposition of proteins and cells in arrays of microwells. Langmuir. 2001. 17: 2828-2834.*
Y. Ito et al., "Preparation of a Protein Micro-Array Using a Photo-Reactive Polymer for a Cell-Adhesion Assay", Biomaterials, vol. 24, 2003, pp. 3021-3026.
T. H. Park et al., "Integration of Cell Culture and Microfabrication Technology", Biotechnol. Prog., vol. 19, 2003, pp. 243-253.
S. F. Abu-Absi et al., "Structural Polarity and Functional Bile Canaliculi in Rat Hepatocyte Spheroids", Experimental Cell Research, vol. 274, 2002, pp. 56-67.
J. Xu et al., "Characterisation of Some Cytotoxic Endpoints Using Rat Liver and HepG2 Spheroids as in Vitro Models and Their Application in Hepatotoxicity Studies. I. Glucose Metabolism and Enzyme Release as Cytotoxic Markers", Toxicology and Applied Pharmacology, vol. 189, 2003, pp. 100-111.
J. M. Kelm et al., "Method for Generation of Homogeneous Multicellular Tumor Spheroids Applicable to a Wide Variety of Cell Types", Biotechnology and Bioengineering, vol. 83, No. 2, Jul. 20, 2003, pp. 173-180.
S. K. Kang et al., "Neurogenesis of Rhesus Adipose Stromal Cells", Journal of Cell Science vol. 117, 2004, pp. 4289-4299.
L. A. Kuns-Schughart et al., "Proliferative Activity and Tumorigenic Conversion: Impact on Cellular Metabolism in 3-D Culture", Am J Physiol Cell Physiol, vol. 278, 2000, pp. C765-C780.
K. E. A. LaRue et al., "Microenvironmental Regulation of Proliferation in Multicellular Spheroids Is Mediated Through Differential Expression of Cyclin-Dependent Kinase Inhibitors", Cancer Research, vol. 64, Mar. 1, 2004, pp. 1621-1631.
S. Kyuwa et al., "Characterization of Embryonic Stem-Like Cell Lines Derived from Embryoid Bodies", Exp. Anim., vol. 46, No. 1, 1997, pp. 11-16.

\* cited by examiner

*Primary Examiner* — Allison Ford
*Assistant Examiner* — Susan E Fernandez
(74) *Attorney, Agent, or Firm* — Oliff PLC (57) ABSTRACT

A microchip is provided that forms cellular tissues having uniform shapes and sizes and that can culture the formed cellular tissues for long periods of time.

The cellular tissue microchip comprises a plurality of cell-retaining cavities (12) for retaining cells, wherein a bottom surface (20) of the cell-retaining cavities has one adhesive region (30) that exhibits cellular adhesiveness and a non-adhesive region (32) that surrounds the adhesive region (30) and that exhibits cellular non-adhesiveness.

11 Claims, 5 Drawing Sheets

FIG.6

US 8,652,847 B2

```
                        SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Sequence of cell adhesion peptide

<400> SEQUENCE: 1

Arg Gly Asp Ser Ala Ala Ala Ala Ala Cys
1               5                   10
```

CELLULAR TISSUE MICROCHIP AND METHOD OF FORMING CELLULAR TISSUE

TECHNICAL FIELD

The present invention relates to a microchip for retaining cells and particularly relates to the formation of cellular tissue.

BACKGROUND ART

Numerous developments that employ cell-culture techniques in medical technology, pharmaceuticals, and the like are currently underway. As a specific example, techniques for culturing cells that express the characteristic functions of biological tissues and organs are being applied to drug toxicity tests, evaluations of endocrine disruption effects, the screening of new drugs, and other techniques, wherein the cultured cells are used as an in vitro model of the tissue or organ.

Such cell-culture techniques generally involve attaching and then culturing cells in a monolayer (i.e., in two dimensions) on a planar substrate on which collagen or another cellular-adhering material has been coated. When primary hepatocytes or the like isolated from the liver of a living organism, for example, are cultured in such a monolayer, the cells in such instances lose the characteristic liver functions or die off in an extremely short period of time.

By contrast, it has been discovered in recent years that the survival and characteristic liver functions of primary hepatocytes can be maintained for longer periods of time by culturing the cells in cellular tissues, which are aggregates wherein the cells are connected one another in three dimensions, instead of culturing the cells in a monolayer.

An example of a conventional method for forming such hepatic cellular tissue is disclosed in Patent Document 1, wherein a specific growth factor is added to the culture medium, whereby spherical hepatic cellular tissues are formed within the pores of a polyurethane foam.

Patent Document 2 discloses the formation of hepatic cellular tissue on a surface that is coated with a polymeric material that is composed of a monomer containing phenylborate, a monomer containing an amino group, and a 2-hydroxyethyl methacrylate copolymer.

[Patent Document 1] Japanese Laid-open Patent Publication No. 10-29951
[Patent Document 2] Japanese Patent Publication No. 3020930

DISCLOSURE OF THE INVENTION

Problems to be Solved by the Invention

In the conventional methods above, however, the formed cellular tissues are of nonuniform shape and size. Therefore, when, for example, an evaluation is made of the metabolic function of a specific drug in the cells, obtaining reliable results has been difficult because, e.g., the number of cells in contact with the drug (in particular, the number of cells near the surface of the cellular tissue) differs for each cellular tissue.

The conventional methods above also involve the use of culture-substrate surfaces to which cells adhere relatively weakly (i.e., which have relatively poor cellular adhesiveness) and the formed cellular tissues are desorbed from the culture-substrate surfaces to be suspended in the culture medium. Therefore, when removing the culture medium from which the nutrients have been consumed and pouring a fresh culture medium or other operations are performed in the culturing process, for example, cells and cellular tissues will therefore be removed along with the culture medium, and culturing may be unable to continue thereafter.

The present invention was made in light of the these problems, and it is one of the objects thereof to provide a microchip that forms cellular tissues having uniform shapes and sizes and that can culture the formed cellular tissues for long periods of time, and to provide a method for forming cellular tissues that uses this microchip.

Means for Solving the Problem

In order to solve these problems, a cellular tissue microchip according to an embodiment of the present invention comprises a plurality of cell-retaining cavities for retaining cells, wherein a bottom surface of the cell-retaining cavities contains one adhesive region that exhibits cellular adhesiveness; and a non-adhesive region that surrounds the adhesive region and that exhibits cellular non-adhesiveness.

A method for forming cellular tissues according to an embodiment of the present invention comprises culturing cells within the cell-retaining cavities of the cellular tissue microchip; and forming a cellular tissue on the adhesive region.

Effect of the Invention

According to the present invention, a microchip can be provided that forms cellular tissues having uniform shapes and sizes and that enables the culture of the formed cellular tissues for long periods of time, and a method for forming cellular tissues can be provided that uses this microchip.

BEST MODE FOR CARRYING OUT THE INVENTION

A cellular tissue microchip according to an embodiment of the present invention will be described below with reference to the drawings. The cellular tissue microchip according to the present invention is not limited to the embodiment below.

Figure 1:
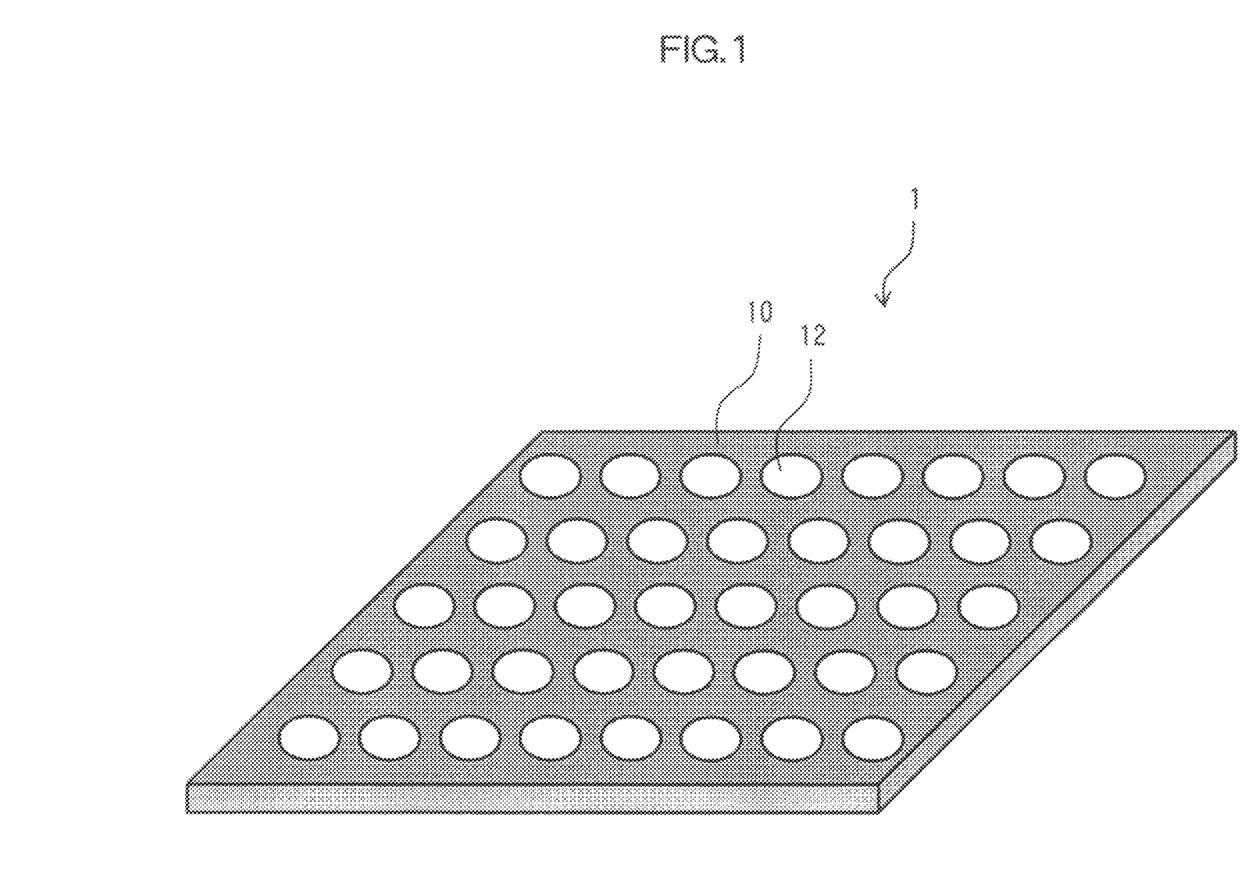
FIG. 1 is descriptive diagram of a cellular tissue microchip according to an embodiment of the present invention.

FIG. 1 is a descriptive diagram of the cellular tissue microchip (referred to below as "the present microchip 1") according to the present embodiment. As shown in FIG. 1, the present microchip 1 has a plurality of cell-retaining cavities 12 that are formed as bottomed holes on a substrate 10 and that have prescribed depths in order to retain cells.

A culture medium into which cells have been dispersed is introduced into the cell-retaining cavities 12 of the present microchip 1. A bottom surface 20 (see FIGS. 2 and 3) of the cell-retaining cavities 12 is used as a culture-substrate surface for the cells, whereby cellular tissues are formed from the cells.

As long as the cells to be formed into cellular tissues are cells that form mutual connections one another, the source of the cells may be any type of animal, organ, tissue, or the like. As specific examples, the cells may be primary cells isolated from the liver, pancreas, kidney, nerves, skin, or other regions of humans, pigs, dogs, rats, mice, or other animals; embryonic stem (ES) cells; cells from established cell lines; or cells resulting from genetic modifications thereof. A single type of cell may be used, or two or more types of cells mixed in any ratio may also be used.

The culture medium used may have any composition as long as the medium is an aqueous solution that includes the necessary salts, nutrients, and other components at appropriate concentrations so that the survival, functionality, and other aspects of the cells can be maintained. As specific examples, the culture medium used may be DMEM (Dulbecco's Modified Eagle's Medium), another basal medium to which antibiotics have been added, or so-called physiological saline solution.

The substrate 10 of the present microchip 1 is composed of, e.g., polystyrene, polyethylene, polypropylene, polycarbonate, polyamide, polyacetal, polyester (polyethylene terephthalate or the like), polyurethane, polysulfone, polyacrylate, polymethacrylate, polyvinyl, a silicone or other synthetic resin, EPDM (ethylene propylene diene monomer) or another synthetic or natural rubber, glass, ceramic, or stainless steel or another metallic material. The substrate 10 is formed into, e.g., a plate shape.

The cell-retaining cavities 12 can be formed in the substrate 10 using any machining method selected in accordance with the material and other properties of the substrate 10. As specific examples, the cell-retaining cavities 12 may be formed on the substrate 10 by punching using a machining center or the like, optical micromachining using a laser or the like, etching, or embossing. Alternatively, the cell-retaining cavities 12 may be formed when the substrate 10 is molded using injection molding, press molding, stereolithography, or the like.

By using such machining methods, the cell-retaining cavities 12 can be formed as, e.g., bottomed holes on the surface of the substrate 10, which has a prescribed thickness, wherein the depth of the bottomed holes is less than the thickness of the substrate 10. The cell-retaining cavities 12 may also be formed by, e.g., forming holes that pass through the substrate 10 and then affixing another member to one surface of the substrate 10 in order to make the bottom surface. As an example, a substrate, film, or other article made from a material that is the same as or different from the material of the substrate 10 in which the through-holes are formed may be used as the member for forming the bottom surface of the cell-retaining cavities 12.

The cell-retaining cavities 12 are positioned in order at prescribed intervals on the substrate 10, as shown in FIG. 1. The ordered plurality of cell-retaining cavities 12 may be formed using a machining center or the like that precisely controlls the machining location according to a computer-aided design (CAD) program.

Figure 2:
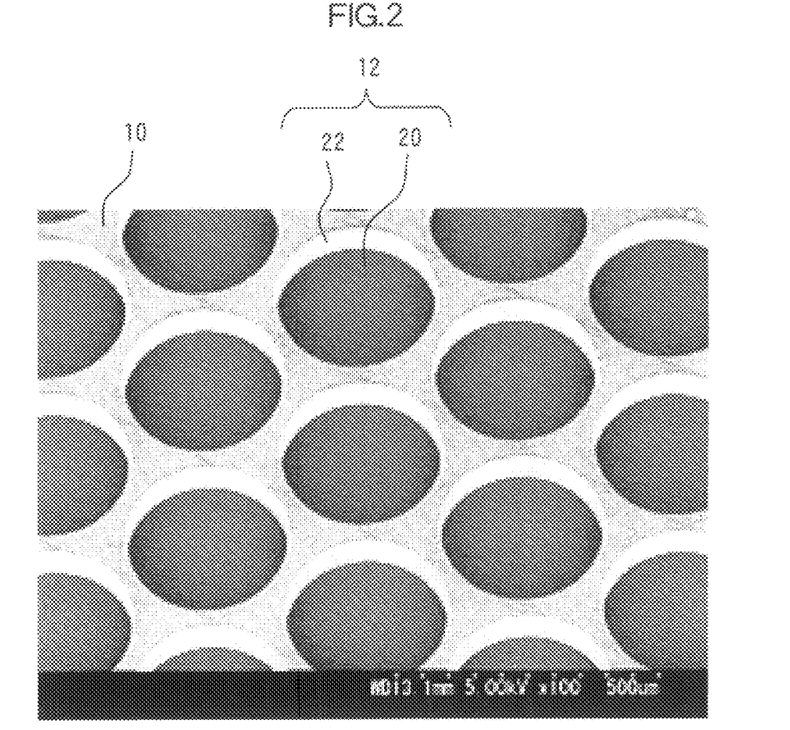
FIG. 2 is an electron microphotograph of cell-retaining cavities according to an embodiment of the present invention.

FIG. 2 is a scanning electron microphotograph that shows a portion of the present microchip 1. As shown in FIG. 2, each of the cell-retaining cavities 12 formed on the substrate 10 have the bottom surface 20 and a lateral surface 22 that form the hole structure. The bottom surface 20 and the lateral surface 22 of each of the cell-retaining cavities 12 have a substantially smooth surface, as shown in FIG. 2.

The shape of the bottom surface 20 is not particularly limited and may be, e.g., a circular shape as shown in FIG. 2, or an ellipsoid, polygon, or other shape. The diameter of the bottom surface 20 is preferably within the range of approximately 2 to 50 times the diameter of the cells to be used, and a range of approximately 4 to 30 times the cell diameter is particularly preferable. The size of the cells changes according to the type, state, and other properties of the cells, and therefore the area of the bottom surface 20 cannot be categorically defined, but a range of, e.g., 100 to $1\times10^6$ $\mu m^2$ is preferable, and a range of 300 to $3\times10^5$ $\mu m^2$ is particularly preferable.

These ranges are stipulated because the cells that are seeded on the bottom surface 20 (i.e., the cells that are seeded within each of the cell-retaining cavities 12) form a cellular tissue on the bottom surface 20, and therefore the size of the bottom surface 20 will dictate the number of cells contained in the cellular tissue formed on the bottom surface 20. Specifically, when the size of the bottom surface 20 is less than the aforementioned lower limit, the number of cells necessary to form a cellular tissue on the bottom surface 20 cannot be retained. When the bottom surface 20 is larger than the aforementioned upper limit, the number of cells to be retained on the bottom surface 20 is too large, and therefore an enormous cellular tissue will be formed. In this case, the cells located inside the cellular tissue are not able to receive adequate quantities of nutrients and oxygen from the culture medium outside the cellular tissue and may die off.

The depth of the cell-retaining cavities 12 is preferably within the range of approximately 1 to 50 times the diameter of the cells to be used, and a range of approximately 2 to 30 times the cell diameter is particularly preferable. This range is stipulated because when the depth of the cell-retaining cavities 12 is less than the aforementioned lower limit, the cells will tend not to be reliably retained within the cell-retaining cavities 12. When the depth of the cell-retaining cavities 12 is greater than the aforementioned upper limit, the amount of oxygen and nutrients provided to the cells on the bottom surface 20 of the cell-retaining cavities 12 may be insufficient.

Figure 3:
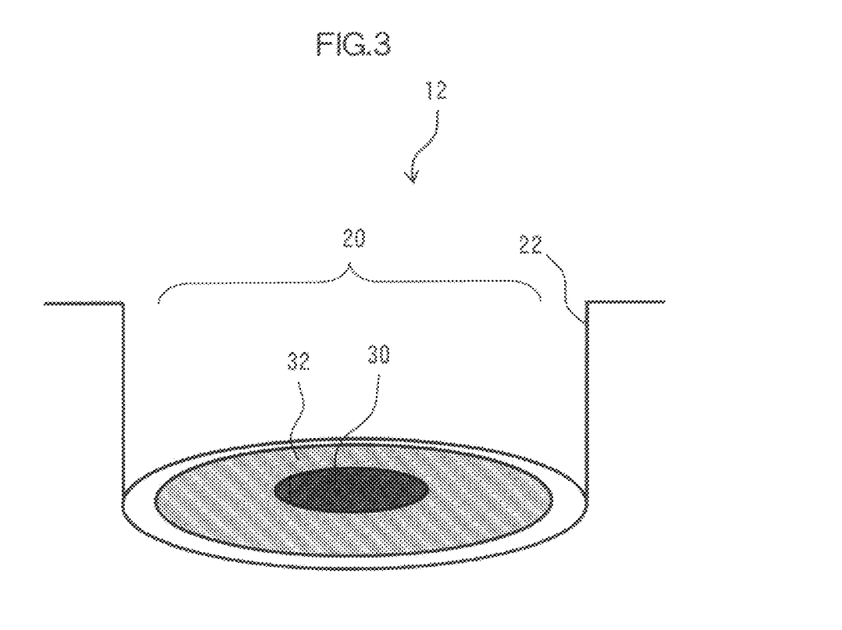
FIG. 3 is a descriptive diagram of a bottom surface of a cell-retaining cavity according to an embodiment of the present invention.

FIG. 3 is a descriptive diagram of one of the plurality of cell-retaining cavities 12 included in the present microchip 1. As shown in FIG. 3, the bottom surface 20 of the cell-retaining cavities 12 has one adhesive region 30 that exhibits cellular adhesiveness and a non-adhesive region 32 that surrounds the adhesive region 30 and that exhibits cellular non-adhesiveness.

The adhesive region 30 has, e.g., a cellular adhesive surface that has an electrically charged state, and a hydrophilicity or a hydrophobicity that are appropriate for cell adhesion within a culture medium or other solution. A cellular adhesive surface refers to, e.g., a surface to which cells can adhere in a relatively flat shape after deforming from a spherical shape when precipitating out of the culture medium onto the surface.

Specifically, the surface of the adhesive region 30 can be formed of, e.g., the material surface itself of the substrate 10 that is exposed as the bottom surface 20 of the cell-retaining cavities 12 when the cell-retaining cavities 12 are formed. The surface of the adhesive region 30 can also be formed of the surface of the exposed substrate 10, e.g., on which a cellular adhesive material that is acquired from living organisms or synthesized, or a material derived therefrom is fixed.

As an example, a material that can bind to a specific protein or other cell surface molecule (e.g., integrin or a sugar receptor) on the cell membrane of the cells to be used may be employed as the cellular adhesive material fixed in place to the adhesive region 30.

As specific examples, collagen, fibronectin, laminin, and the like may be used as cellular adhesive materials that are acquired from living organisms. Compounds wherein, e.g., a desired functional group, polymer, or the like has been bonded (e.g., covalently bonded using a condensation reaction or the like) to such cellular adhesive materials may be used as derivatives of these materials.

Compounds that include specific amino acid sequences (e.g., arginine-glycine-aspartate (RGD) sequences), specific sugar sequences (e.g., galactose side chains), or the like that exhibit cellular adhesiveness may be used as synthetic materials having good cellular adhesiveness. Compounds wherein, e.g., a desired functional group, polymer, or the like has been bonded to such cellular adhesive materials may be used as derivatives of these materials.

The aqueous solution of the cellular adhesive material and the like is dried on the bottom surface 20, for example, whereby these cellular adhesive materials that are acquired from living organisms or synthesized, or the derivatives thereof can be fixed in place to the bottom surface 20. Chemical reactions may also be made to occur in the aqueous solution of the cellular adhesive material and the like between the functional groups of the cellular adhesive material and the functional groups of the bottom surface 20 (e.g., a condensation reaction between carboxyl groups and amino groups or the like), forming covalent bonds and the like whereby the cellular adhesive material can be fixed in place to the bottom surface 20.

Meanwhile the non-adhesive region 32 has, e.g., a surface that has poor cellular adhesiveness and that has an electric charge state, and a hydrophilicity or a hydrophobicity that are not suitable for cell adhesion such that the cells within the culture medium are substantially unable to adhere the surface. A surface that exhibits cellular non-adhesiveness is a surface wherein, e.g., when cells precipitate out of the culture medium onto the surface, the shape of the cells does not deform substantially from a spherical shape, so that extremely weak adhesion results, but the cells are easily desorbed by currents and the like in the culture medium. Alternatively, the cells are completely unable to adhere to the surface and are maintained in a suspneded state with a spherical shape in the culture medium.

Specifically, the surface of the non-adhesive region 32 can be formed of, e.g., the material surface itself of the substrate 10 that is exposed as the bottom surface 20 of the cell-retaining cavities 12 when the cell-retaining cavities 12 are formed. The surface of the non-adhesive region 32 can also be formed of the surface of the exposed substrate 10, e.g., on which a cellular adhesive material that is acquired from living organisms or synthesized, or a material derived therefrom is fixed.

As an example, a cellular non-adhesive material that is synthetic or biologically derived and that does not bind to proteins, sugar chains, or other cell surface molecules on the cell membrane of the cells to be used may be employed as the material having poor cellular adhesiveness that is fixed in place to the non-adhesive region 32.

As a specific example, albumin, other proteins exhibiting high hydrophilicity, or the like can be used as biologically derived cellular non-adhesive materials. Compounds wherein, e.g., a desired functional group, polymer, or the like has been bonded to such cellular non-adhesive materials may be used as derivatives of these materials.

Polyethylene glycol or other polymers that exhibit extremely high hydrophilicity, MPC (2-methacryloyloxy-ethyl phosphorylcholine), poly-HEMA (poly-hyroxyethyl methacrylate), SPC (segmented polyurethane), or the like can be used as synthetic materials having poor cellular adhesiveness. Compounds wherein, e.g., a desired functional group, polymer, or the like has been bonded to such cellular non-adhesive materials may be used as derivatives of these materials.

The aqueous solution of the cellular non-adhesive material and the like is dried on the bottom surface 20, for example, whereby these cellular non-adhesive materials that are acquired from living organisms or synthesized, or the derivatives thereof can be fixed in place to the bottom surface 20. Chemical reactions may also be made to occur in the aqueous solution of the cellular non-adhesive material and the like between the functional groups of the cellular non-adhesive material and the functional groups of the bottom surface 20, forming covalent bonds and the like whereby the cellular non-adhesive material can be fixed in place to the bottom surface 20.

The adhesive region 30 may also be formed in the vicinity of the center of the bottom surface 20 of the cell-retaining cavities 12. If the cell-retaining cavities 12 are positioned in an ordered fashion on the present microchip 1, as shown in FIG. 1, the cellular tissues formed on the adhesive regions 30 of the bottom surfaces 20 of the cell-retaining cavities 12 in such instances can also be positioned in an ordered fashion on the present microchip 1, and the shapes of the formed cellular tissues can be made uniform.

Therefore, when the cellular tissues are, e.g., stained using a fluorescent dye or the like and the function of the cellular tissues is evaluated according to the extent of staining or the like, the positions of the uniformly shaped cellular tissues can be accurately specified according to the coordinates or the like established on the present microchip 1. The extent of staining can therefore be quickly, easily, and accurately analyzed using an automatic analyzer or the like.

The bottom surface 20 that comprises the adhesive region 30 and the non-adhesive region 32 may be formed as a entirely flat surface, as shown in FIG. 3, or may be formed to have a step or the like on a portion of at least one of the regions or between the adhesive region 30 and the non-adhesive region 32.

A summary of a method of forming cellular tissues using the present microchip 1 will described next. First, the cells to be used are dispersed in the culture medium at a prescribed density. A prescribed volume of the solution into which the cells have been dispersed is then introduced into each of the cell-retaining cavities 12, whereby the cells are seeded. The cells are thereby made to precipitate out onto the bottom surface 20 of the cell-retaining cavities 12.

The number of cells seeded in one cell-retaining cavity 12 is preferably set so that the cells that have precipitated out onto the bottom surface 20 can contact each other to the extent necessary to form mutual connections, and so as to limit the size of the cellular tissue, which is formed by the aggregation of the cells to be within the prescribed range.

As a specific example, the number of seeded cells per cell-retaining cavity 12 is preferably within a range of 2 to $1.5 \times 10^5$, and a range of 50 to $3.0 \times 10^4$ is particularly preferable. The number of seeded cells per unit area on the bottom surface 20 of the cell-retaining cavity is preferably within the range of 30 to $1.5 \times 10^4$ cells/mm$^2$.

These ranges are stipulated because at least two cells must be retained per cell-retaining cavity 12 in order to form a cellular tissue. Additionally, if the number of seeded cells is too large, the cellular tissue formed from those cells will be enormous, and the internal cells may be subject to necrosis due to lack of nutrients and oxygen.

Next, the present microchip 1 onto which the cells have been thus seeded is kept horizontal and maintained in a stationary state for a prescribed period of time, whereby the cells are cultured. During the stationary culture period, among the cells that have precipitated out onto the bottom surfaces 20 of the cell-retaining cavities 12, the cells that have precipitated out on the adhesive region 30 adhere to the surface of the adhesive region 30. The cells that precipitate out on the non-adhesive region 32 are maintained in a suspended state without adhering to the surface of the non-adhesive region 32, or adhere extremely weakly.

The stationary culture is further maintained, or culturing is continued while the present microchip 1 is shaken so that an arc will be drawn on the horizontal surface. The cells that have precipitated out on the bottom surfaces 20 of the cell-retaining cavities 12 will thereby connect one another as the culture period progresses. As a result, the cells gradually move so as to gather on the adhesive regions 30 of the bottom surfaces 20, and cellular tissues in which the cells have connected in three-dimensions are formed on the adhesive regions 30. These cellular tissues are not suspended in the culture medium and can be cultured for long periods of time in a state that the cells adhere to the adhesive regions 30 being stably retained within the cell-retaining cavities 12.

A flow inlet for the influx of the culture medium to the cell-retaining cavity 12 and a flow outlet for the efflux of the culture medium from the cell-retaining cavity 12 can be also formed on a portion of the lateral surface 22 of each of the cell-retaining cavities 12 of the present microchip 1, whereby the culture can be performed while flowing the culture medium within the cell-retaining cavities 12 after the cellular tissues have been formed on the adhesive region 30.

Working Example

An example wherein cellular tissues are formed using the present microchip 1 will be described next.

[Cellular Tissue Microchip Manufacture]

A flat plate (24 mm×24 mm, 200 µm thick) of polymethyl methacrylate was used as the substrate 10 of the present microchip 1 of the present example. Specifically, a machining center (a table-top NC micromachining apparatus; PMT Corporation) was used to punch holes in a 10 mm-square rectangular area on a portion of the surface of the polymethyl methacrylate plate, whereby approximately 1000 circular through-holes were formed having a diameter of 300 µm. The circular through-holes were positioned in an ordered fashion so that the distance between the centers of the through-holes was 400 µm.

A flat plate (22 mm×22 mm, 400 µm thick) of glass was used as the bottom surface 20 of the cell-retaining cavities 12 of the present microchip 1. Specifically, a sputtering apparatus (E-1030; Hitachi, Ltd.) was used to perform sputtering in a 12 mm-square rectangular area on a portion of the surface of the glass plate, whereby a thin film (9 nm thick) of platinum (Pt) was formed. The platinum-surface portion of the glass plate was aligned with the portion of the polymethyl methacrylate plate on which the through holes had been formed, and a silicone adhesive (TSE389; GE Toshiba Silicones Co., Ltd.) was used to bond together the glass plate and the polymethyl methacrylate plate. The cell-retaining cavities 12 were thus formed as shown in FIG. 2 having depths of 200 µm and having circular bottom surfaces 20 that had diameters of 300 µm.

Meanwhile, a stamp of PDMS (poly (dimethyl siloxane)) having a plurality of cylindrical protrusions, which had diameters of 100 µm and lengths of 200 µm, was manufactured by mold pressing. The positions of the cylindrical protrusions of the stamp were established so that the distance between the centers of the circular cross-sections on the ends of the protrusions was 400 µm so as to correspond with the locations of the cell-retaining cavities 12 on the present microchip 1. The adhesive regions 30 were formed on the bottom surfaces 20 of the cell-retaining cavities 12 by microcontact printing using this stamp as described hereinafter.

Specifically, a peptide containing a cellular adhesive RGD sequence (amino acid sequence: RGDSAAAAAC; Thermo Electron Corporation) was prepared as the cellular adhesive material to be fixed in place to the surface of the adhesive regions 30. The ends of the cylindrical protrusions of the manufactured stamp were immersed in a DMSO (dimethyl sulfoxide) solution containing the cellular adhesive peptide at a concentration of 1.78 mg/mL, whereby the solution of the peptide was applied to the end surfaces of the cylindrical protrusions.

During observation with phase-contrast microscopy, the positions of the cylindrical protrusions of the stamp to which the peptide solution was applied were then aligned with the areas near the centers of the bottom surfaces 20 of the cell-retaining cavities 12 of the present microchip 1 on which the platinum was deposited. The ends of the cylindrical protrusions were then pressed onto the bottom surfaces 20, whereby the peptide solution applied to the ends of the cylindrical protrusions was coated on the areas near the centers of the bottom surface 20 of the cell-retaining cavities 12. The peptide solution was dried in a nitrogen atmosphere. Chemical bonds were thereby formed between the platinum surface of the bottom surfaces 20 and the thiol groups included on the cysteines on the ends of the cellular adhesive peptide molecules, and the cellular adhesive peptides were fixed in place to the platinum surface.

One adhesive region 30 having a diameter of approximately 100 µm and upon which the cellular adhesive peptide was fixed was thereby formed in vicinity of the center of the bottom surface 20 of each of the cell-retaining cavities 12, which had diameters of 300 μm.

The non-adhesive region 32 was formed in the following manner on the bottom surface 20 that includes the adhesive region 30. Specifically, a synthetic, cellular non-adhesive polymer (chemical formula: $CH_3(CH_2CH_2)_nSH$; Nektar Therapeutics) having a polyethylene glycol (PEG) chain of molecular weight 5000 was prepared as the cellular non-adhesive material to be fixed in place to the surface of the non-adhesive region 32.

An excess amount of ethanol solution containing the cellular non-adhesive polymer at a concentration of 25 mg/mL was added to the cell-retaining cavities 12 in which the adhesive region 30 had been formed. A chemical bond was then formed in a nitrogen atmosphere between the platinum surface of the bottom surface 20 and the thiol group included in the cellular non-adhesive polymer, whereby the cellular non-adhesive polymer was fixed in place to the platinum surface (i.e., on the region of the bottom surface 20 excluding the adhesive region 30). The entirety of the present microchip 1 was then washed thoroughly using an ethanol solution and the excess cellular non-adhesive polymer was removed. The present microchip 1 was then sterilized by being immersed in ethanol for approximately two hours.

The present microchip 1 was thus manufactured having the adhesive region 30 formed in the vicinity of the center of the bottom surface 20 of each of the cell-retaining cavities 12 and having the non-adhesive region 32 formed in the regions other than the adhesive region 30. The present microchip 1 was used in the culture experiment below.

[Cell Preparation]

Primary hepatocytes that were prepared from rat liver using a well-known collagenase perfusion method were used as the cells in the present example. The method for preparing these hepatocytes is briefly described. Specifically, a cannula was first inserted into the portal vein (one of the blood vessels that connects to the liver) of a 7-week-old Wistar-strain rat (body weight 250 g). A blood-removal solution having a prescribed composition was injected into the liver from the cannula, after which a digestive solution was perfused into which collagenase (Wako Pure Chemical Industries, Ltd.) had been dissolved at a concentration of 0.5 mg/mL, and digestion was carried out to break the mutual connections and the like between the hepatocytes in the liver. The digested liver was then excised and hepatocytes in which the individual cells were dispersed and isolated were obtained by diffusion treatments using a scalpel, pipette, and the like and by washing using a culture medium and the like.

A serum-free culture medium that was used as the culture medium was prepared by adding 60 mg/L of proline (Sigma-Aldrich), 50 mg/mL of epidermal growth factor (EGF; Funakoshi Co., Ltd.), 7.5 mg/L of hydrocortisone (Wako Pure Chemical Industries, Ltd.), 0.1 μM of copper sulfate 5-hydrate (Wako Pure Chemical Industries, Ltd.), 3 μg/L of selenate (Wako Pure Chemical Industries, Ltd.), 50 μM of zinc sulfate 7-hydrate (Wako Pure Chemical Industries, Ltd.), 50 μg/L of linoleic acid (Sigma), 58.8 mg/L of penicillin (Meiji Seika Kaisha, Ltd.), 100 mg/L of streptomycin (Meiji Seika Kaisha, Ltd.), 1.05 g/L of sodium bicarbonate (Wako Pure Chemical Industries, Ltd.), and 1.19 g/L of 2-[4-(2-hydroxyethyl)-1-piperazine] ethanesulfonic acid (HEPES; Dojindo Laboratories) to 13.5 g/L of Dulbecco's Modified Eagle's Medium (DMEM; GIBCO).

[Formation of Cellular Tissue]

The resulting hepatocytes were dispersed in the culture medium to a density of $5.0 \times 10^5$ cells/mL. The sterilized present microchip 1 was mounted on the bottom part of a polystyrene culture vessel (diameter 35 mm; Falcon). A 2.0 mL portion of the solution into which the cells were dispersed was added to the present microchip 1 and cultured at 37° C. in a stationary state in an atmosphere of 5% carbon dioxide gas and 95% air.

As a first control experiment, a flat plate (22 mm×22 mm, 400 μm thick) of glass, which was identical to the glass plate used to form the bottom surface 20 of the cell-retaining cavities of the present microchip 1, was mounted on the bottom part of a polystyrene culture vessel having a diameter of 35 mm. Another 2.0 mL portion of the solution into which the cells were dispersed was then added onto the glass plate and cultured in a stationary state in the same manner.

As a second control experiment, a flat plate (22 mm×22 mm, 400 μm thick) of glass, which was identical to the glass plate used to form the bottom surface 20 of the cell-retaining cavities of the present microchip 1 and on which collagen (Cellmatrix Type I-C, Nitta Gelatin, Inc.) was coated, was mounted on the bottom part of a polystyrene culture vessel having a diameter of 35 mm. Another 2.0 mL portion of the solution into which the cells were dispersed was then added onto the collagen-coated glass plate and cultured in a stationary state in the same manner. The culture medium within the culture vessels used for the present microchip 1 and the control experiments was replaced with fresh culture medium every other day after the start of the culture.

Figure 4:
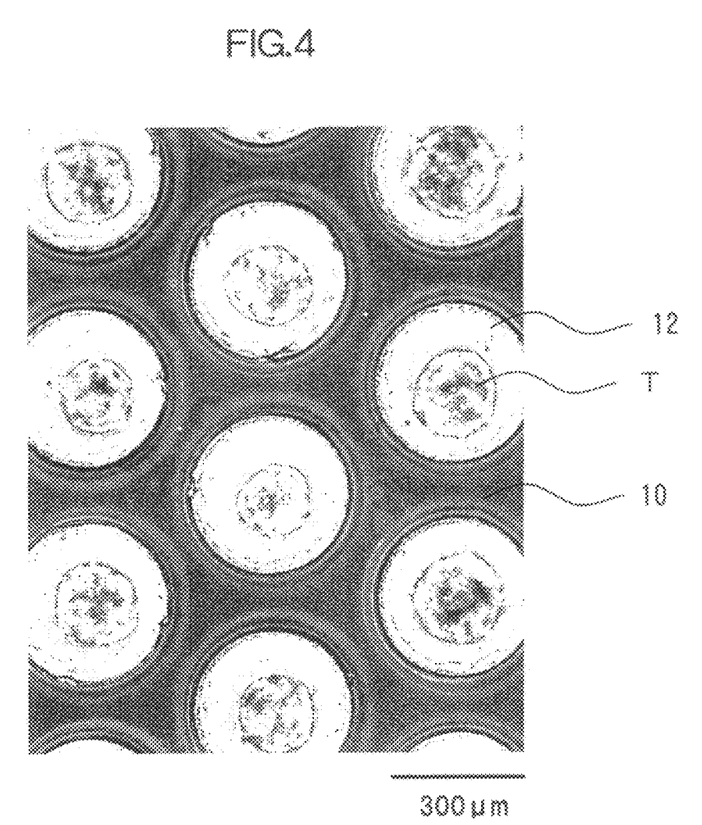
FIG. 4 is a phase-contrast microphotograph of hepatic cellular tissues formed on the cellular tissue microchip according to an embodiment of the present invention.

FIG. 4 shows a phase-contrast microphotograph of the hepatic cellular tissues (T in FIG. 4) formed in the cell-retaining cavities 12 on the third day of the culture. One hepatic cellular tissue is formed in each of the cell-retaining cavities 12, as shown in FIG. 3. The shapes of the cellular tissues are all spherical and have smooth surfaces. Such spherical hepatic cellular tissues were formed in the cell-retaining cavities 12 of the present microchip 1 within one to two days after the start of the culture.

Each of the hepatic cellular tissues were formed in the vicinity of the center of the bottom surface 20 within each of the cell-retaining cavities 12, as shown in FIG. 3. Specifically, each of the hepatic cellular tissues adhered to the adhesive region 30 on the bottom surface 20 of each of the cell-retaining cavities 12 and were stably retained without being suspended in the culture medium. Hepatocytes were not substantially present on the non-adhesive region 32.

On the other hand, hepatic cellular tissues of various sizes and irregular shapes were formed from a portion of the seeded cells in the first control experiment, and the tissues were in a suspended state within the culture medium over the entirety of the glass plate (not shown). Additionally, the hepatocytes adhered to the collagen-coated glass plate in the second control experiment were flattened and extended in a monolayer state (not shown).

Figure 5:
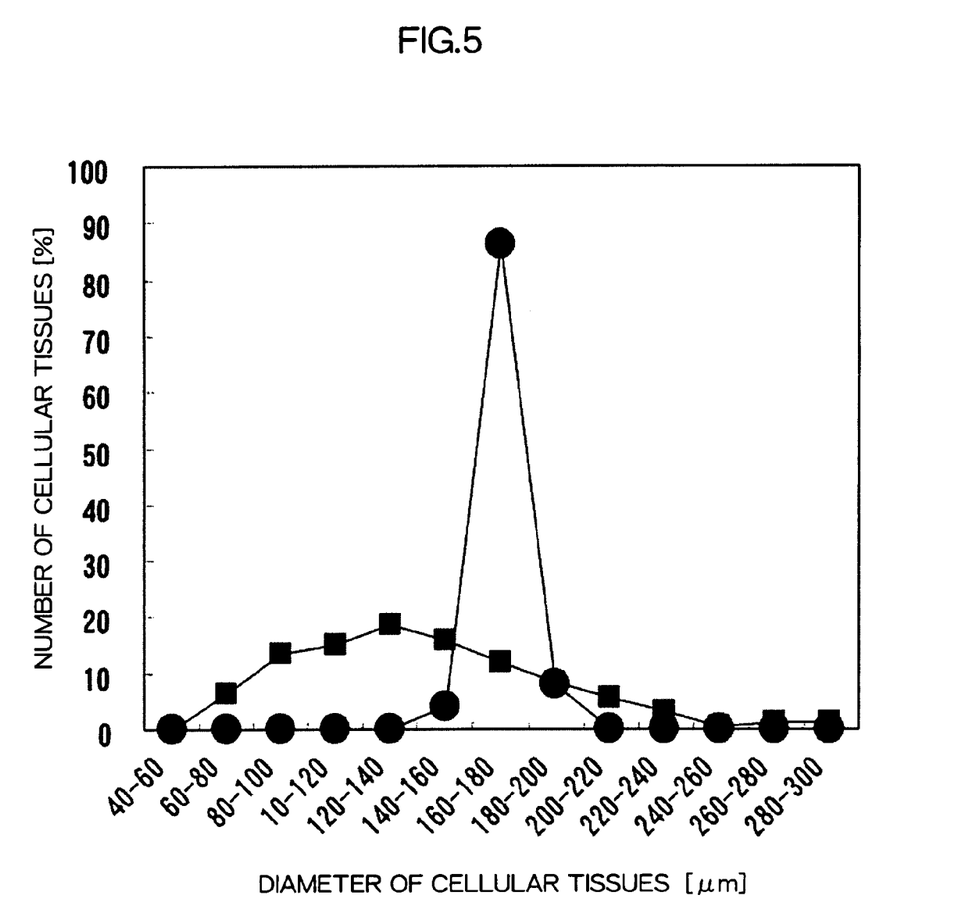
FIG. 5 is a histogram that shows the distribution of particle diameter of the hepatic cellular tissues formed on the cellular tissue microchip according to an embodiment of the present invention.

FIG. 5 is a histogram that shows the particle diameter distributions of the hepatic cellular tissues formed in the cell-retaining cavities 12 of the present microchip 1 and of the hepatic cellular tissues formed in the first control experiment. The horizontal axis in FIG. 5 designates the diameter (μm) of the hepatic cellular tissues. The vertical axis designates the ratio (%) of the number of hepatic cellular tissues having the diameter shown at each point on the horizontal axis relative to the total number of hepatic cellular tissues of which particle diameter was measured. The circles in FIG. 5 designate the results for the hepatic cellular tissues formed using the present microchip 1, and the squares designate the results for the hepatic cellular tissues formed in the first control experiment.

The diameters of 86% of the hepatic cellular tissues among those formed in the present microchip 1 were within the range of 160 to 180 μm, as shown in FIG. 5. In other words, hepatic cellular tissues having similar particle diameters and extremely uniform sizes were formed in the cell-retaining cavities 12 of the present microchip 1.

On the other hand, the hepatic cellular tissues formed in the first control experiment had a variety of particle diameters and had sizes that were non-uniform overall. The measurement of the particle diameters of the hepatic cellular tissues was carried out by image analysis of the microscopy results.

The ability to remove ammonia (one of the waste substances within living organisms), which is one of the characteristic detoxification functions of the liver, was also evaluated for the hepatic cellular tissues formed in the present microchip 1 and for the monolayer of hepatocytes in the second control experiment. For evaluating the ability to remove ammonia, on the third, seventh, tenth, and fourteenth days after the start of the culture, the culture medium within the culture vessel containing the hepatic cellular tissues or the monolayer of hepatocytes was first replaced with a culture medium to which ammonia at a prescribed concentration had been added, and culturing was then continued. The ammonia-added culture medium was then recovered after a prescribed period of time had elapsed, and the amount of decrease in the concentration of ammonia in the recovered culture medium during the prescribed period of time after the addition of ammonia was measured using a commercially available measurement kit (Wako Pure Chemical Industries, Ltd.).

Figure 6:
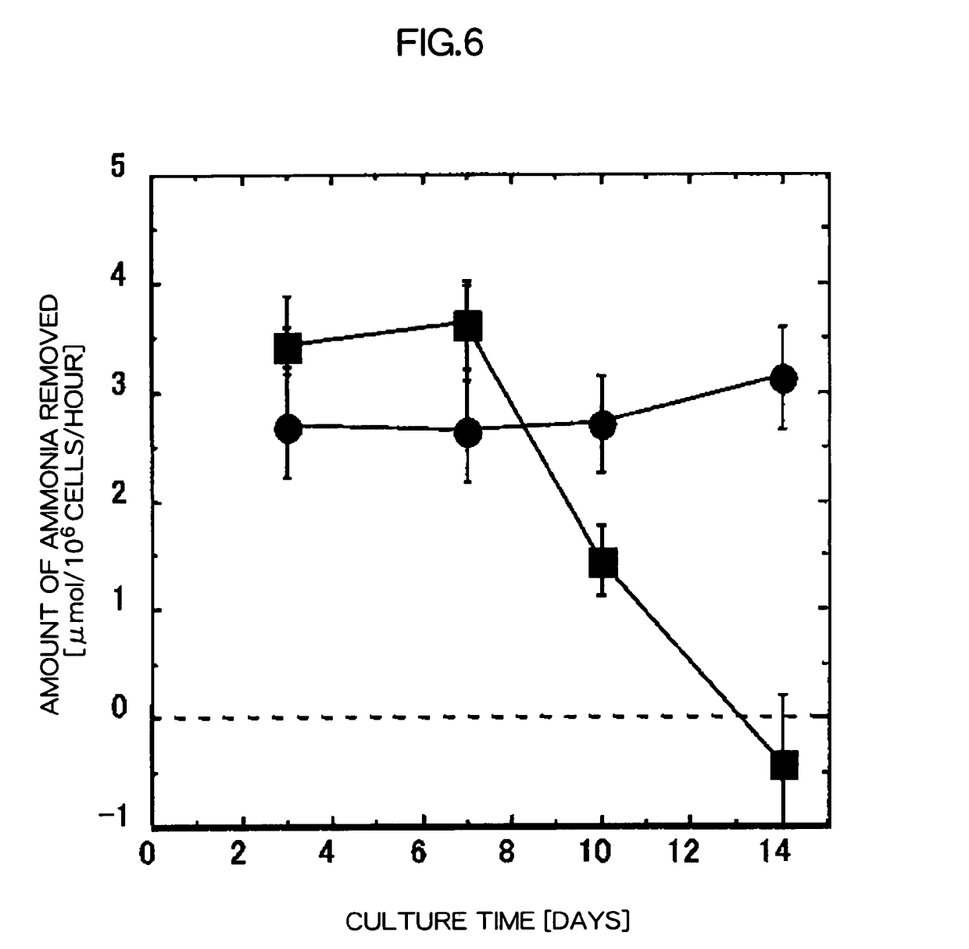
FIG. 6 is a graph that shows the results of evaluating the liver function of the hepatic cellular tissues formed on the cellular tissue microchip according to an embodiment of the present invention.

FIG. 6 shows the results of evaluating the ability to remove ammonia. The horizontal axis in FIG. 6 designates the culture time (the number of days cultured). The vertical axis designates the amount of ammonia removed (μmol) per unit number of cells ($10^6$ cells) and per unit time (hours). The circles in FIG. 6 designate the results for the hepatic cellular tissues formed using the present microchip 1, and the squares designate the results for the monolayer of hepatocytes of the second control experiment.

As shown in FIG. 6, the hepatic cellular tissues formed in the present microchip 1 continued to express the ability to remove ammonia for the two weeks after the start of the culture. On the other hand, the ability of the monolayer of hepatocytes in the second control experiment to remove ammonia monotonically decreased after the first week of the culture and had completely disappeared at the two-week point. The hepatic cellular tissues formed in the first control experiment were in a suspended state, and most of the hepatic cellular tissues would be removed when replacing the culture medium or performing similar actions. Evaluating the ability of these hepatic cellular tissues in the first control experiment to remove ammonia was therefore difficult.

By using the present microchip 1 in this manner, hepatic cellular tissues that continue to express specific liver functions at a high level were able to be cultured for long periods of time in a state that the hepatic cellular tissues were stably fixed in the vicinity of the center of the bottom surface 20 of the cell-retaining cavities 12.

The invention claimed is:

1. A cellular tissue microchip for forming cellular tissues from cells that are capable of forming mutual connections, the cellular tissue microchip comprising:
   a plurality of cell-retaining cavities for retaining the cells, wherein an area of a bottom surface of the cell-retaining cavities is within a range of $1 \times 10^2$ to $1 \times 10^6$ μm$^2$; and
   the bottom surface consists of:
   one adhesive region that exhibits cellular adhesiveness; and
   a non-adhesive region that surrounds the adhesive region and that exhibits cellular non-adhesiveness.

2. The cellular tissue microchip of claim 1, wherein the adhesive region is formed in a vicinity of a center of the bottom surface of the cell-retaining cavities.

3. The cellular tissue microchip of claim 1, wherein a diameter of the bottom surface of the cell-retaining cavities is within a range of 2 to 50 times a diameter of the cells.

4. The cellular tissue microchip of claim 1, further comprising a cellular adhesive material fixed to the adhesive region and that is acquired from a living organism or synthesized, wherein, optionally, a functional group or a polymer is bonded to the cellular adhesive material.

5. The cellular tissue microchip of claim 1, further comprising a cellular non-adhesive material fixed to the non-adhesive region and that is acquired from a living organism or synthesized, wherein, optionally, a functional group or a polymer is bonded to the cellular non-adhesive material.

6. The cellular tissue microchip of claim 1, further comprising a cellular tissue that is formed from the cells and that adheres to the adhesive region.

7. The cellular tissue microchip of claim 1, further comprising a cellular adhesive material fixed to the adhesive region selected from the group consisting of collagen, fibronectin, and laminin, wherein, optionally, a functional group or a polymer is bonded to the cellular adhesive material.

8. The cellular tissue microchip of claim 1, further comprising a cellular non-adhesive material fixed to the non-adhesive region, the cellular non-adhesive material comprising an albumin or another protein exhibiting hydrophobicity, or a polymer exhibiting hydrophobicity selected from the group consisting of polyethylene glycol, 2-methacryloyloxyethyl phosphorylcholine, poly-hyroxyethyl methacrylate, and segmented polyurethane, wherein, optionally, a functional group or a polymer is bonded to the cellular non-adhesive material.

9. The cellular tissue microchip of claim 1, wherein a diameter of the adhesive region is from about 100 μm to about 200 μm.

10. A method for forming cellular tissues, comprising:
culturing cells that are capable of forming mutual bonds within the cell-retaining cavities of the cellular tissue microchip of claim 1; and
forming a cellular tissue adhering to the adhesive region.

11. The method of forming cellular tissues of claim 10, wherein the cells are cultured within a range of 2 to $1.5 \times 10^5$ cells per cell-retaining cavity.

* * * * *